(12) United States Patent
Matsumoto et al.

(10) Patent No.: US 6,268,156 B1
(45) Date of Patent: Jul. 31, 2001

(54) CANCER TREATMENTS

(75) Inventors: Sumio Matsumoto, Nagoya; Kenichi Kobayashi, Urawa; Takashi Okamoto, Nagoya, all of (JP)

(73) Assignee: SmithKline Beecham Seiyaku K.K., Tokyo (JP)

( * ) Notice: Subject to any disclaimer, the term of this patent is extended or adjusted under 35 U.S.C. 154(b) by 0 days.

(21) Appl. No.: 09/158,936

(22) Filed: Sep. 22, 1998

Related U.S. Application Data
(60) Provisional application No. 60/059,745, filed on Sep. 23, 1997.

(51) Int. Cl.[7] .................. G01N 33/53; G01N 33/567; G01N 33/48; A01N 43/42; A61K 31/47
(52) U.S. Cl. ................ 435/7.1; 435/7.23; 436/64; 514/300
(58) Field of Search .................... 435/7.1, 7.23; 436/64

(56) References Cited

PUBLICATIONS

Nagano, T et al., Successful treatment of metastatic renal cell carcinoma with cimetidine, Japanese Journal of Urology, vol. 10, pp. 1201–1204, Abstract only, Oct. 1996.*
The 18th Annual Meeting of Cancer Immunological Surgery abstract, Study on the inhibitory Action of H2–Receptor Antagonist on the Metastasis of Cancer, p. 72, May 28, 1997—non certified English translation.
Matsumoto, S. :Lancet 345 p. 115 (1995).
Svendson, et al. Dis. Colon Rectum 38, pp. 514–518 (1995).
Adams, et al. Lancet 344, pp. 1768–1769 (1994).
Hellstrand, et al. Cancer Immunol. Immunother. 9, pp. 416–419 (1994).
Creaga, et al. J. Clin. Oncol. 3, pp. 977–981 (1992).
Sagaster, et al. Ann. Oncol. 6, pp. 999–1003 (1995).
Hahm, et al. Scan. J. Gastroenterol 30, pp. 265–271 (1985).
Nakamori, et al. Cancer Res., 53, pp 3632–3637 (1995).
Takeda, et al. Biochem. Biopha. Res. Comm. 179, pp. 713–719 (1991).
Garcia–Caballero, et al. Adv.Bioscience. 69, pp. 273–287 (1993).
Hansbrough, et al. An. J. Surg. 151, pp. 249–255 (1986).
Katoh, et al. Lancet 348, pp. 404–405 (1996).
Kimura, et al. Inorg. Chem. 25, pp. 2242–2246 (1986).

* cited by examiner

Primary Examiner—Anthony C. Caputa
Assistant Examiner—Jennifer Hunt
(74) Attorney, Agent, or Firm—Dara L. Dinner; Stephen Venetianer; Charles M. Kinzig

(57) ABSTRACT

The present invention is to a method of treating cancer in patients in need thereof with an effective amount of cimetidine. Cimetidine has been found to inhibit the expression of E-selectin, the ligands of sialyl Lewis X and sialyl Lewis A antigen-bearing cancer cells are incapable of attaching to a vascular wall. The present invention has found that cimetidine inhibits metastasis in patients whose specimens stained strongly for sialyl Lewis X and sialyl Lewis A antigens.

8 Claims, 12 Drawing Sheets

SURVIVAL CURVE (KAPLAN-MEIER METHOD)

Metastatic Characteristics

| Location | cimetidine | control |
|---|---|---|
| liver | 3 | 3 |
| lung | 2 | 7 |
| bone | 0 | 1 |
| brain | 0 | 2 |
| anastomosis, local | 2 | 5 |
| paraaortic lymph node | 0 | 2 |
| left supra-clavicular LN | 0 | 1 |
| peritoneum | 1 | 1 |
| ovarium | 0 | 1 |
| | 8 | 23 |

FIG. 12

CANCER TREATMENTS

This application claims priority to U.S. Provisional application 60/059,745, filed Sep. 23, 1997.

FIELD OF THE INVENTION

This invention relates to a new medical use of cimetidine, compositions therefor, and a new method of diagnosis.

BRIEF DESCRIPTION OF THE DRAWINGS

FIG. 12 Table 1 Metastatic characteristics.

SUMMARY OF THE INVENTION

Figure 1:
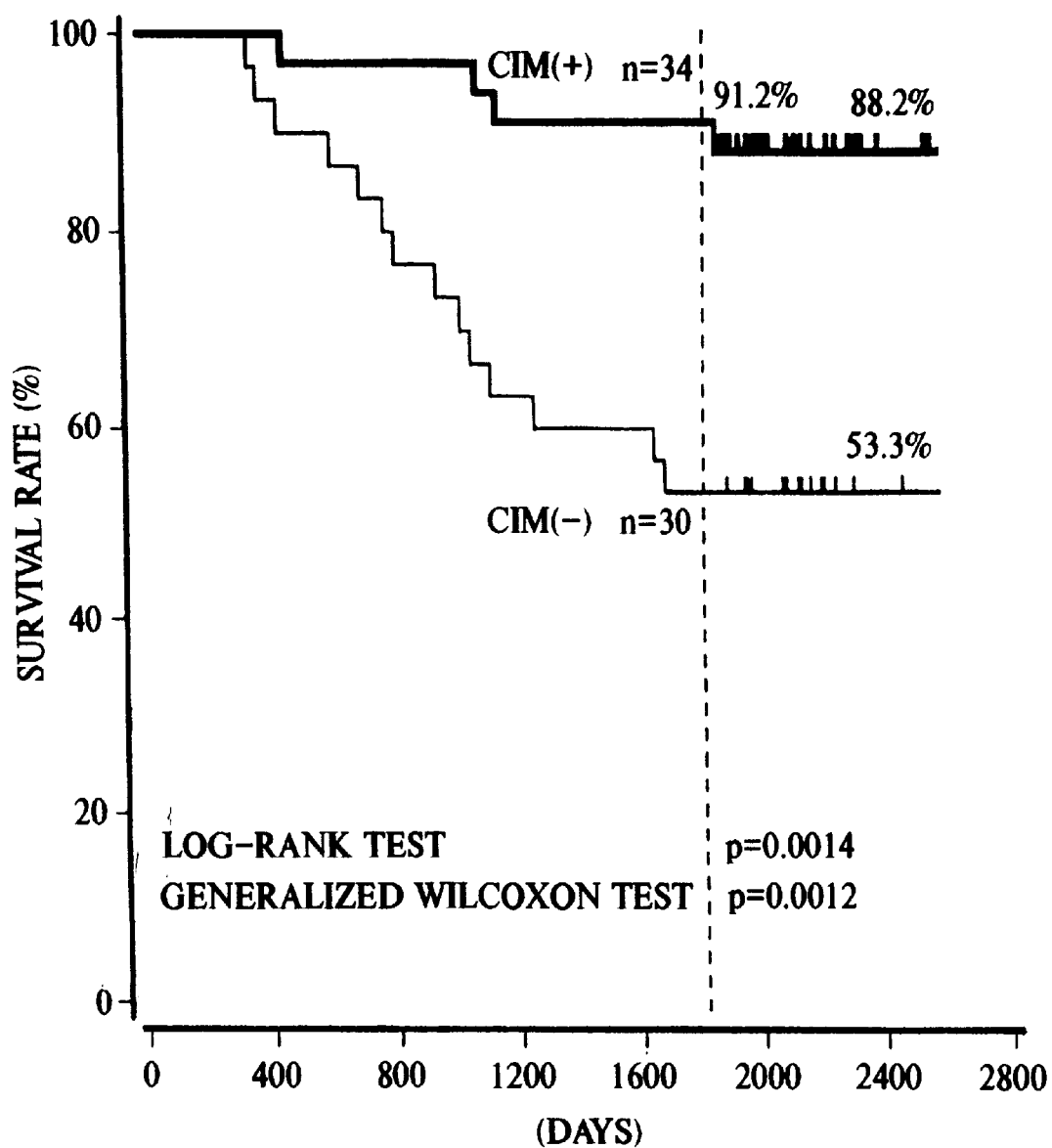
FIG. 1 Survival curves of the enrolled patients. Kaplan-Meier life table method.

The present invention is to a method of preventing metastasis of cancers in subjects bearing sialyl Lewis antigens X and A which method comprises the administration of cimetidine in an effective amount to prevent metastasis.

Another aspect of the present invention is a method of diagnosing cancer patients whom might benefit from cimetidine treatment which method comprises testing said patients for the presence of sialyl Lewis X and A antigens.

Another aspect of the present invention is a method of treating cancer in a patient in need thereof, which method comprises testing patients for the presence of sialyl Lewis X and A antigens, and treating patients who stain positively for said antigens with cimetidine in an effective amount to prevent metastasis.

A preferred group of cancers for treatment herein includes colorectal cancer, gastric cancer, liver cancer, renal cancer, cystic cancer, pulmonary cancer, biliary tract cancer, pancreatic cancer, uterine cancer, ovarian cancer, breast cancer or melanoma.

Another aspect of the present invention is a method of treating a cancer in a patient in need thereof, which patient has underwent curative resection, which method comprises administering to said patient an effective amount of cimetidine.

DETAILED DESCRIPTION OF THE INVENTION

It has been found that the presence of cimetidine blocks E-selectin induction without alerting its mRNA level; this blockade is likely to inhibit the adhesion of cancer cells to endothelial cells which is regarded as one of the critical steps of cancer invasion and metastasis.

It has also been found that the E-selectin ligands, sialyl Lewis antigen X and sialyl Lewis antigen A are reliable indicators of which cancer patients are likely to respond to cimetidine treatment.

According to the present invention, a method of preventing metastasis of cancers is provided for, in a subject bearing sialyl Lewis antigens X and A which method comprises the administration of an effective amount of cimetidine. Also provided is a method of diagnosing which cancer patients might benefit from cimetidine treatment by testing patients for the presence of sialyl Lewis X and A antigens. Another aspect of the invention is a method of treating cancers in patients in need thereof, which method comprises testing patients for the presence of sialyl Lewis X and A antigens, and treating patients with an effective amount of cimetidine who stain positively for their presence. This invention also provides for a method of preventing metastasis of cancers by administering an effective amount of cimetidine sufficient to inhibit E-selectin expression.

Preferably the original cancer being treated will be colorectal cancer, gastric cancer, liver cancer, renal cancer, cystic cancer, pulmonary cancer, biliary tract cancer, pancreatic cancer, uterine cancer, ovarian cancer, breast cancer or melanoma.

A particular embodiment of the present invention is the treatment of colorectal cancer patients who have undergone curative resection. In particular, the present invention is to a method of treating cancer in patients who have underwent curative resection, with an effective amount of cimetidine. Another embodiment of the present invention is a method of treating cancer in patients in need thereof, who are the subclass of colorectal cancer patients who have undergone curative resection, with an effective amount of cimetidine.

Preferably the cimetidine will be administered orally. Preferably the oral dose will be from 200 to 1600 mg per day, preferably about 800 mg per day for a 100 kg adult and pro-rata for other weights. Preferably the dose will be given twice a day, with the dose equally divided between the morning and evening. It is recognized that administration may be for at least a year, or more.

Preferably the cimetidine will be initially co-administered (simultaneously or sequentially) with one or more cytotoxic agents. Preferred cytotoxic agents for use herein include, but are not limited to MMC (mitomycin C), and 5-FU. Preferably, a combination of cytotoxic agents is used.

Preferably the cimetidine will be administered as soon as the patient is diagnosed as having cancer and having the specific antigens, ideally before or immediately after surgery to remove a tumor. Preferably the cimetidine therapy will be continued for an extended period, for example from one to twenty four months or for up to five years, or for three to six months after the cancer appears to be in remission, or for one to six months after cytotoxic therapy is discontinued. Other medicaments can be co-administered with the cimetidine on an intermittent or continuous basis: such medicaments include the cyto-toxic agents above, or other agents, such as the interferons, for example IFN-alpha.

It has previously reported about the possible survival benefit that is conferred on colorectal cancer patients when cimetidine therapy was started two weeks postoperatively for one year (Matsumoto, et at., Lancet 345: 115 (1995)). There have been at least two other studies in colorectal cancer, one in which cimetidine was used as a postoperative adjuvant treatment, (Svendson, et al., Dis. Colon Rectum 38, 514–518 (1995)) and the other in which pre- and postoperative short-tern cimetidine administration demonstrated possible survival benefit (Adams, et al. Lancet 344: 1768–1769 (1994)). There have also been reports concerning cimetidine in malignant melanoma and renal cancers (see Hellstrand, et al. Cancer Immunol. Immunother 9, 416–419 (1994); Creaga et al., J. Clin Oncol, 3, 977–981 (1992); and Sagaster, et al., Ann Oncol., 6, 999–1003 (1995)). Other $H_2$ receptor antagonists did not reveal any such clear survival benefit (Hahm, et al. Scand J Gastroenterol 30, 265–271 (1985)). These different effects on survival still remain unclear.

It has now been discovered that cimetidine blocks the expression of E-selectin on the endothelial surface of the human umbilical vein. The ligand of E-selectin was sialyl Lewis X and A antigens (see Nakamori, et al., Cancer Res., 53, 3632–3637 (1993), and Takada et al., Biochem Biophs Res Commun 179, 713–719 (1991)). In the randomized control studies, all study cases have survived for longer than five years.

One aspect of the present invention reveals that that the administration of cimetidine, and the inhibition of metastasis, are correlated to high levels of staining of the sialyl Lewis X and A antigens of cancer cells. Shown below is the results of the discovery.

Survival Benefit Conferred on Cancer Patients by Cimetidine

Advanced colorectal cancer patients (n=64) who underwent curative resection were registered and assorted randomly into two groups, namely the cimetidine and control groups.

Figure 2:
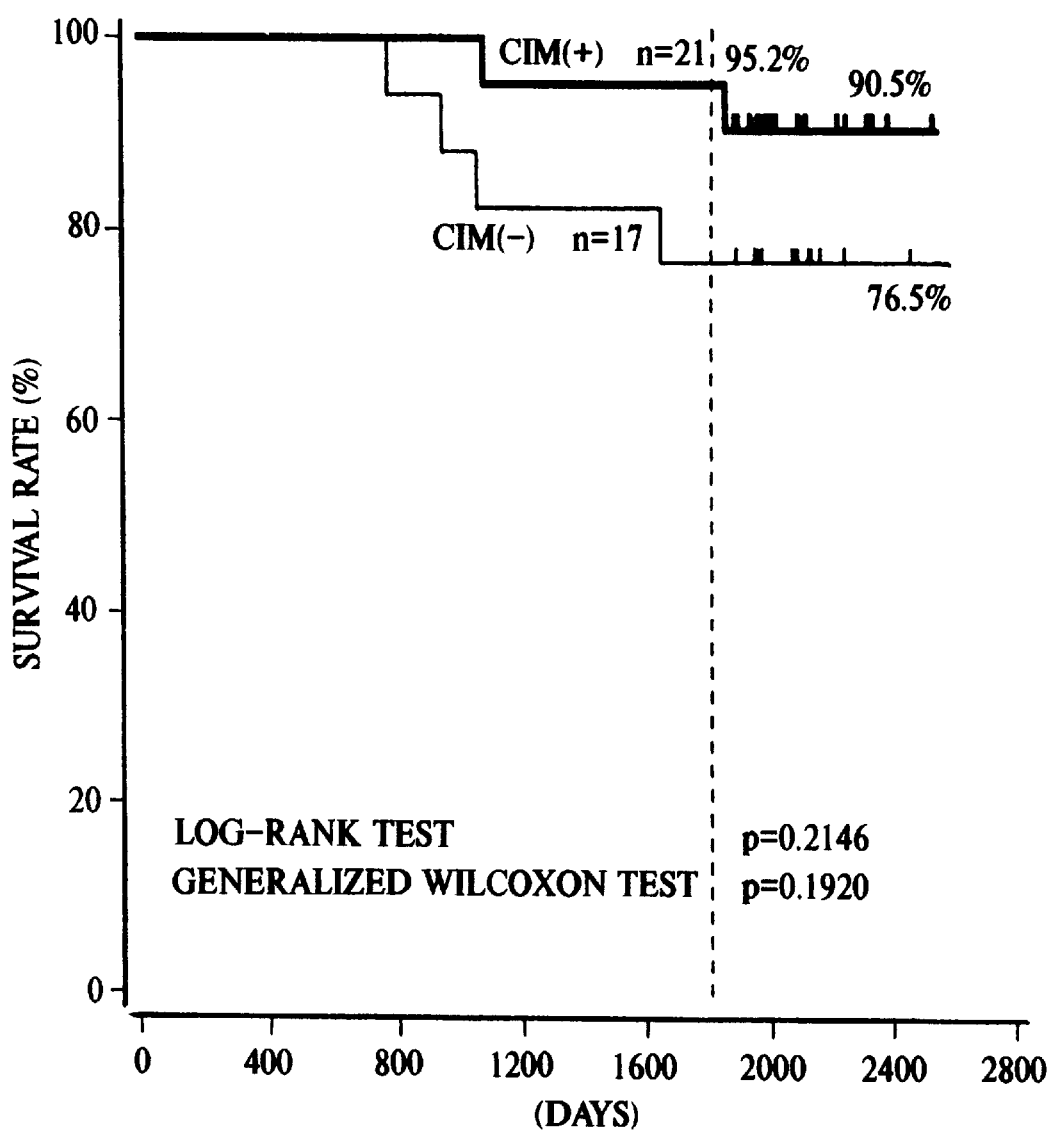
FIG. 2 Survival curve of Dukes A+B. The 5-year survival was not significant between the cimetidine and the control group in Dukes A+B.
Figure 3:
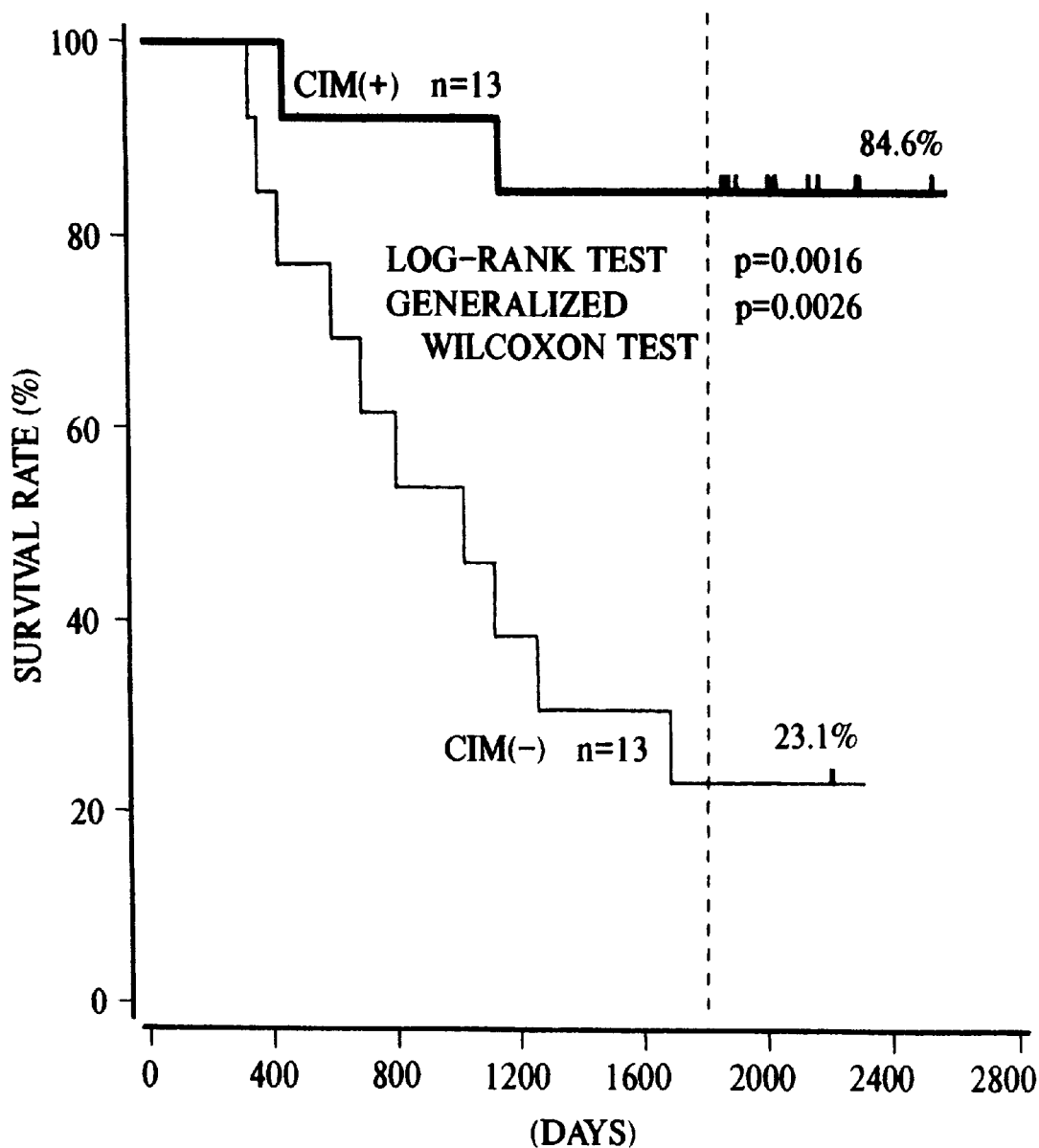
FIG. 3 Survival curve of the Dukes C. The 5-year survival of the cimetidine group was better than that of the 5-Fu group.

Advanced colorectal cancer patients (n=34) received 8 mg/m$^2$ of intravenous MMC within 24 hours postoperatively, and 800 mg/day p.o. of cimetidine and 200 mg/day of 5-FU for one year, starting two weeks following curative operation. The cimetidine group was compared with the control group, who received the same treatment except for cimetidine (n=30). The 5-year survival rate was 91.2% for the cimetidine group and 53.3% for the control group (Log-Rank test: p=0.0014: generalized Wilcoxon test: p=0.0012)(see FIG. 1). Then they were divided into Dukes A+B, and C. The 5-year survival rate was 85.2% for the cimetidine group Dukes A+B and 76.5% for the control group (Log-Rank test: p=0.2146, generalized Wilcoxon test: p=0.1920)(FIG. 2). The 5-year survival rate was 84.6% for the cimetidine Dukes C group and it was 23.1% for the control group (Log-Rank test: p=0.0016, generalized Wilcoxon test: p=0.0026)(FIG. 3).

Inhibition of Metastasis by Cimetidine to Cancer Bearing Sialyl Lewis X or A Antigen The level of immunostaining of cancer cells was graded into four categories: level 0, no staining; level 1.5% or less staining; level 2, 5–70% staining, and level 3, 70% or more staining.

A comparative analysis was made with respect to the level of immunostaining, and of metastasis and treatment.

Occurrence of metastasis was compared between the cimetidine group and the control group. It was found that 7 of 34 patients (8 sites) from the cimetidine group had metastases, while 16 patients had metastases (23 sites) were found in the control group (n=30)(p=0.0060)(Table 1-FIG. 12).

Figure 4:
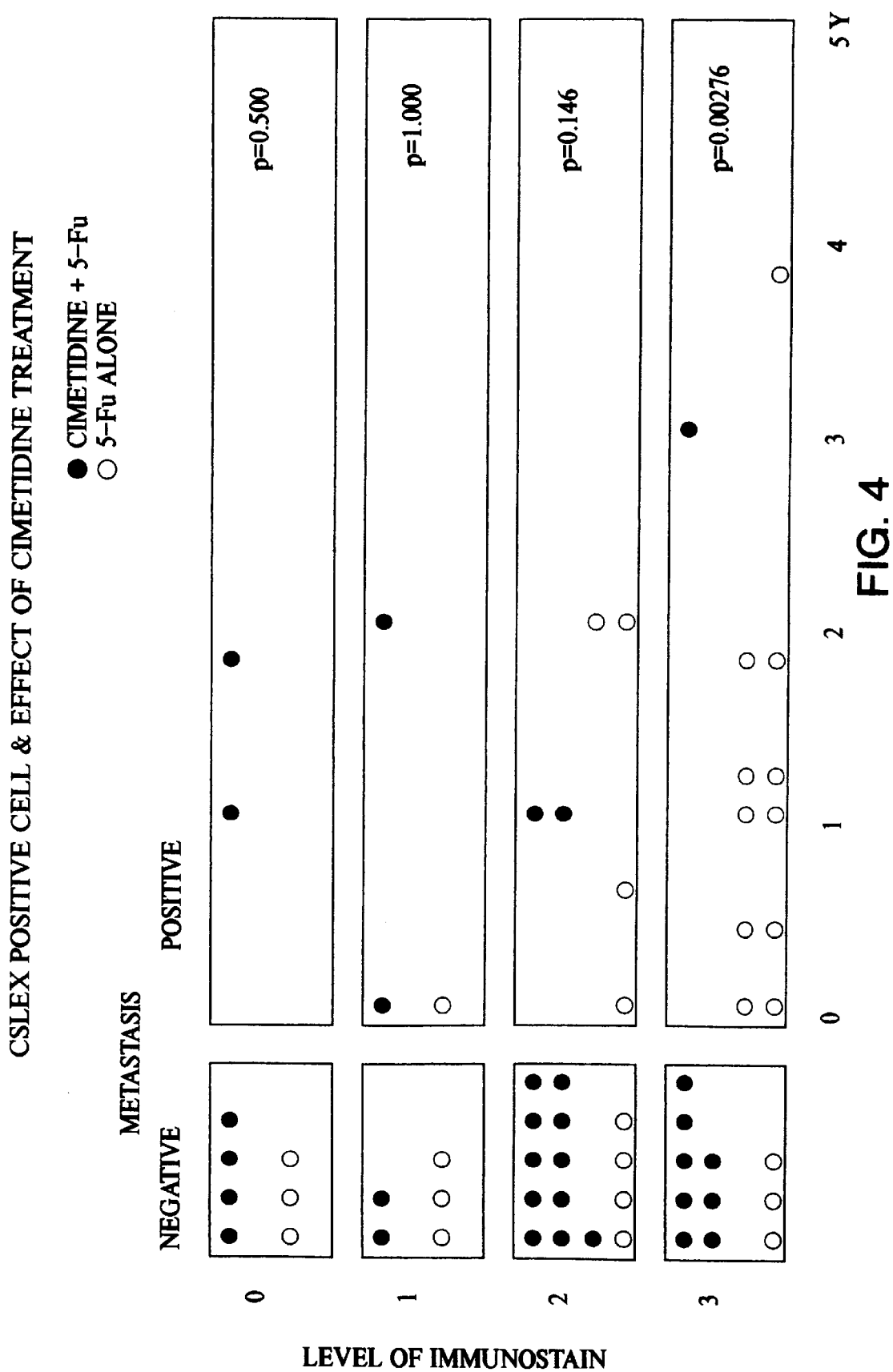
FIG. 4 Anti-sialyl Le* antibody CSLEX positive cell and effect of cimetidine treatment. Cimetidine was significantly effective for level 3 stained cancer cells.

Analysis was made with respect to CSLEX. When those cancer cells had level 2 immunostaining were compared between the cimetidine and the control group, it was found that 2 out of the 13 patients from the cimetidine group had metastasis (15.4%), whereas 11 patients were free of metastasis (84.6%). In the control group, 4 of the 8 patients had metastasis (50.0%), whereas 4 patients were free of metastasis (50.0%)(p=0.146). There were 9 patients in the cimetidine group whose specimens had level 3 staining of whom 1 (11.1%) had metastasis, whereas 8 were free of metastasis (88.9%). In the control group, 14 had level 3 staining of whom 11 (78.6%) had metastasis, whereas 3 (21.4%) were free of metastasis (p=0.00276)(FIG. 4).

Figure 5:
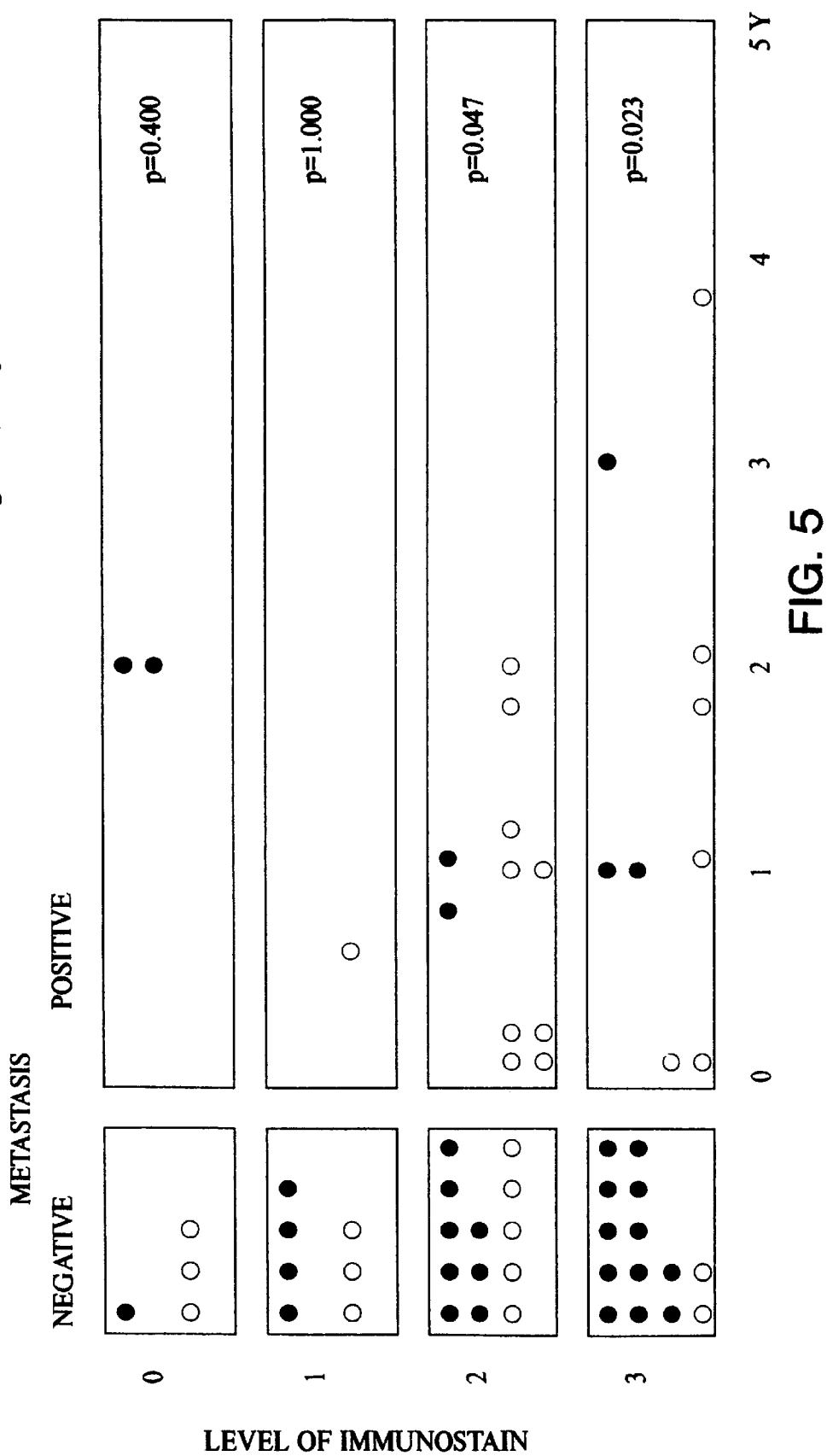
FIG. 5 Anti-sialyl Le* antibody KM93 positive cell and effect of cimetidine treatment. Cimetidine was significantly effective for level 3 stained cancer cells.

The specimens from 10 patients who received cimetidine were graded to be level 2 for KM93, of whom 8 (80.0%) had no metastasis and 2 (20.0%) had metastasis. Upon comparison between the cimetidine group and the control group it was found that, in the control group, 2 patients had metastasis (20.0%), whereas 8 patients were free of metastasis (80.0%)(p=0.047). There were 15 patients whose specimens had level 3 staining of whom 3 (20.0%) had metastasis, whereas 12 were free of metastasis (80.0%) in the cimetidine group. In the control group, 8 had level 3 staining of whom 6 (75.0%) had metastasis, whereas 2 (25.0%) were free of metastasis (n=0.023)(FIG. 5).

Figure 6:
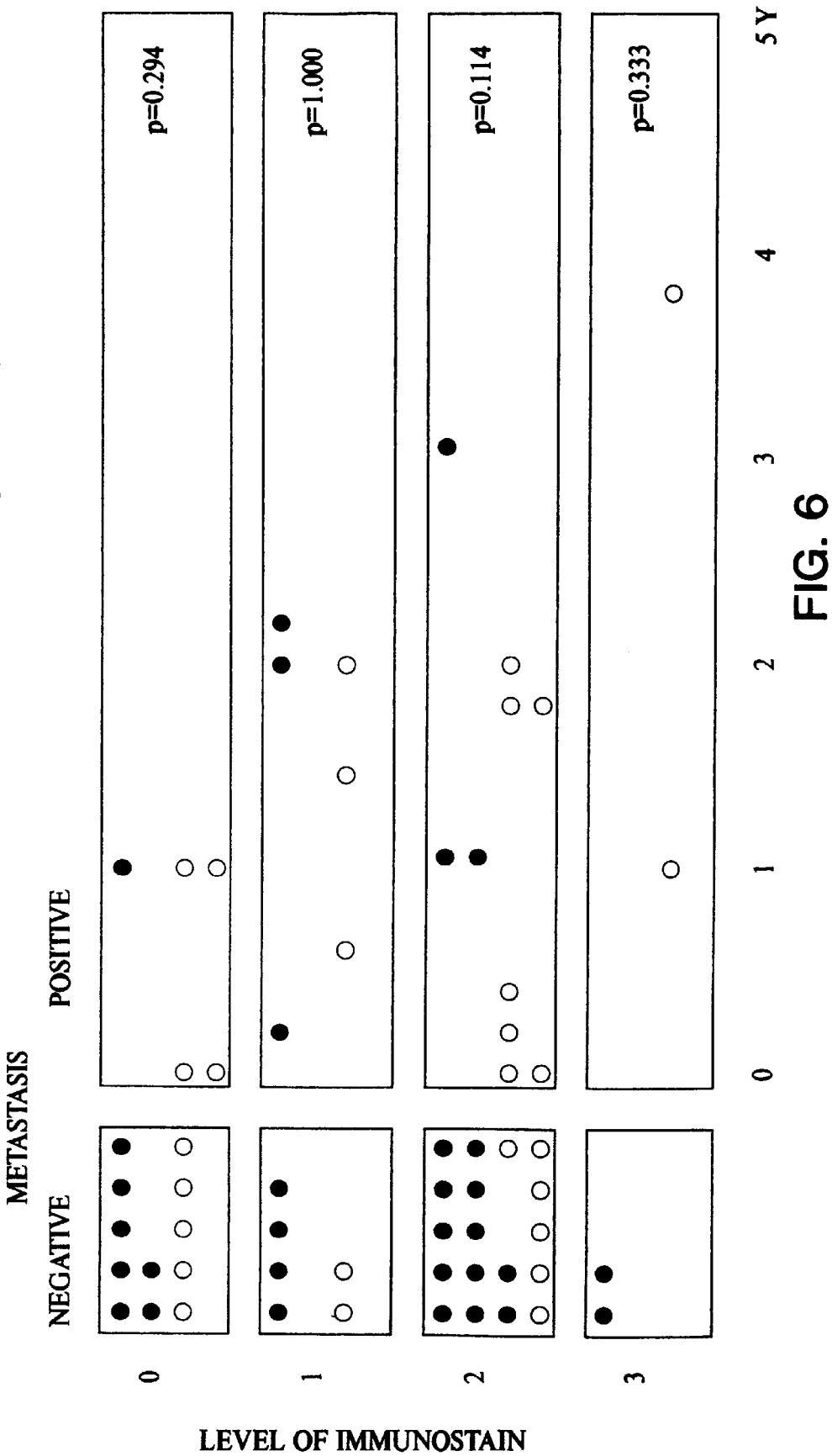
FIG. 6 Anti-sialyl Le* antibody FH6 positive cell and effect of cimetidine treatment. Cimetidine was not statistically significant due to small amount of positively stained cells.

The specimens from 15 patients who received cimetidine were graded to be level 2 for FH6, of whom 12 (80.0%) had no metastasis and 3 (20.0%) had metastasis. There were two specimens from the cimetidine group and they had level 3 staining for FH6; all of these patients were free of metastasis. There were 13 patients in the control group whose specimens had level 2 staining for FH6, of whom 7 (53.3%) had metastasis and 6 (46.2%) were free of metastasis (p=0.114). There were two specimens with level 3 staining for FH6 in the control group and all of these patients had developed metastasis (p=0.333)(FIG. 6).

Figure 7:
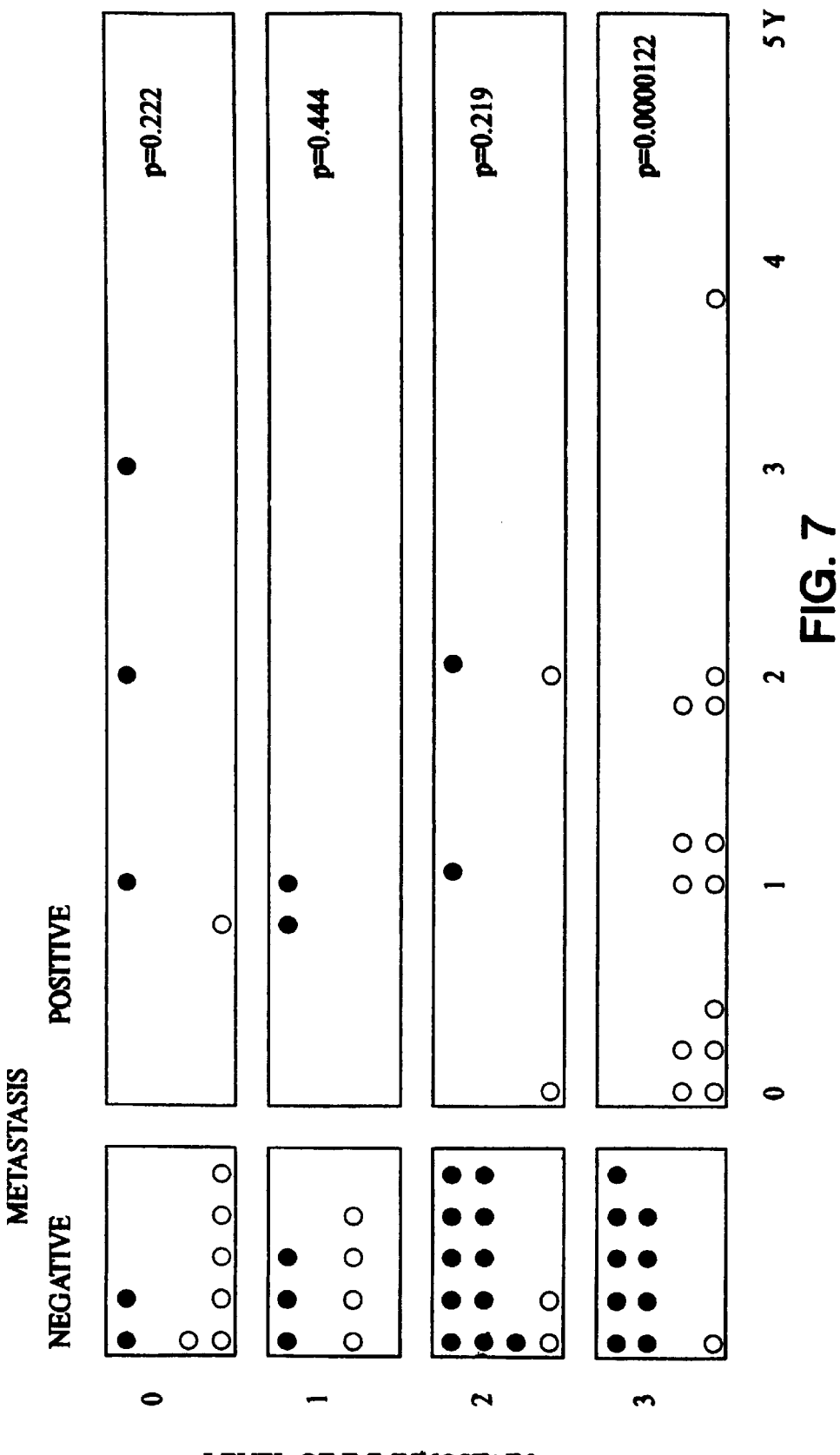
FIG. 7 Anti-sialyl Le* antibody CA 19-9 positive cell and effect of cimetidine treatment. Cimetidine was also significant for level 3CA19-9 stained cancer cells.

Analysis was also made with respect to CA19-9, (sialyl Lewis A) which is another ligand to E-selectin. There were 9 patients who had level 3 staining in the cimetidine group and all of these patients were free of metastasis and one (7.7%) was free of metastasis (p=0.0000122)(FIG. 7).

The above data suggests that cimetidine inhibited metastasis in patients with sialyl-Lewis X and A antigens with levels 2 and 3 immunostaining, whereas many of the control patients with sialyl-Lewis X and A antigens having levels 2 and 3 immunostaining developed metastatic recurrence.

Survival Benefit Conferred on Cancer Stained Strongly for Sialyl-Lewis or A Antigen by Cimetidine The survival was compared at the level 3 staining between the cimetidine and the control group.

Figure 8:
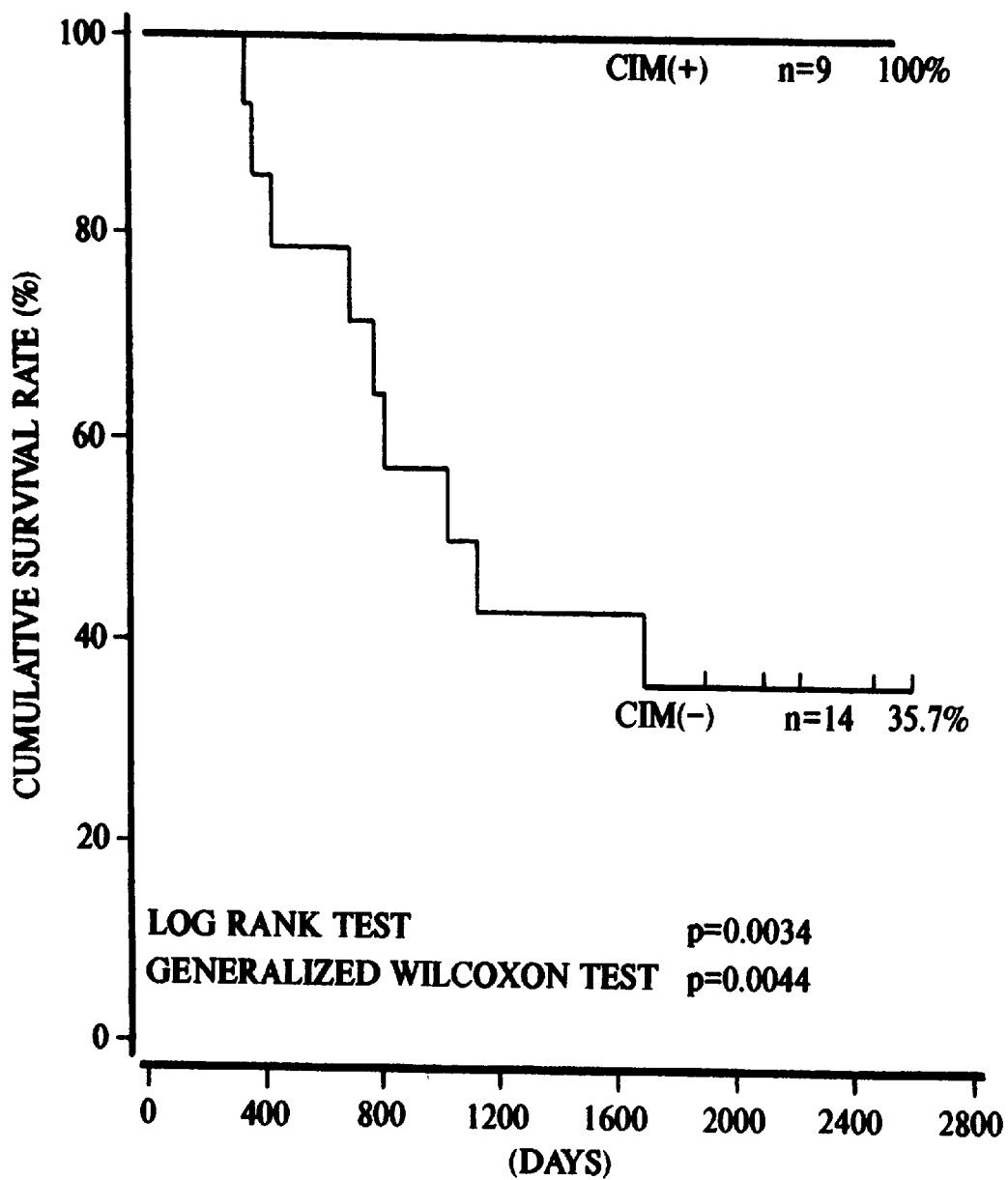
FIG. 8 Cumulative Survival Rate by Kaplan-Meier Method [CSLEX Level=3]

In CSLEX, the 5-year survival rate was 100.0% for the cimetidine group and 35.7% for the control group (Log-Rank test: p=0.0034, generalized Wilcoxon test; p=0.0044) (FIG. 8).

Figure 9:
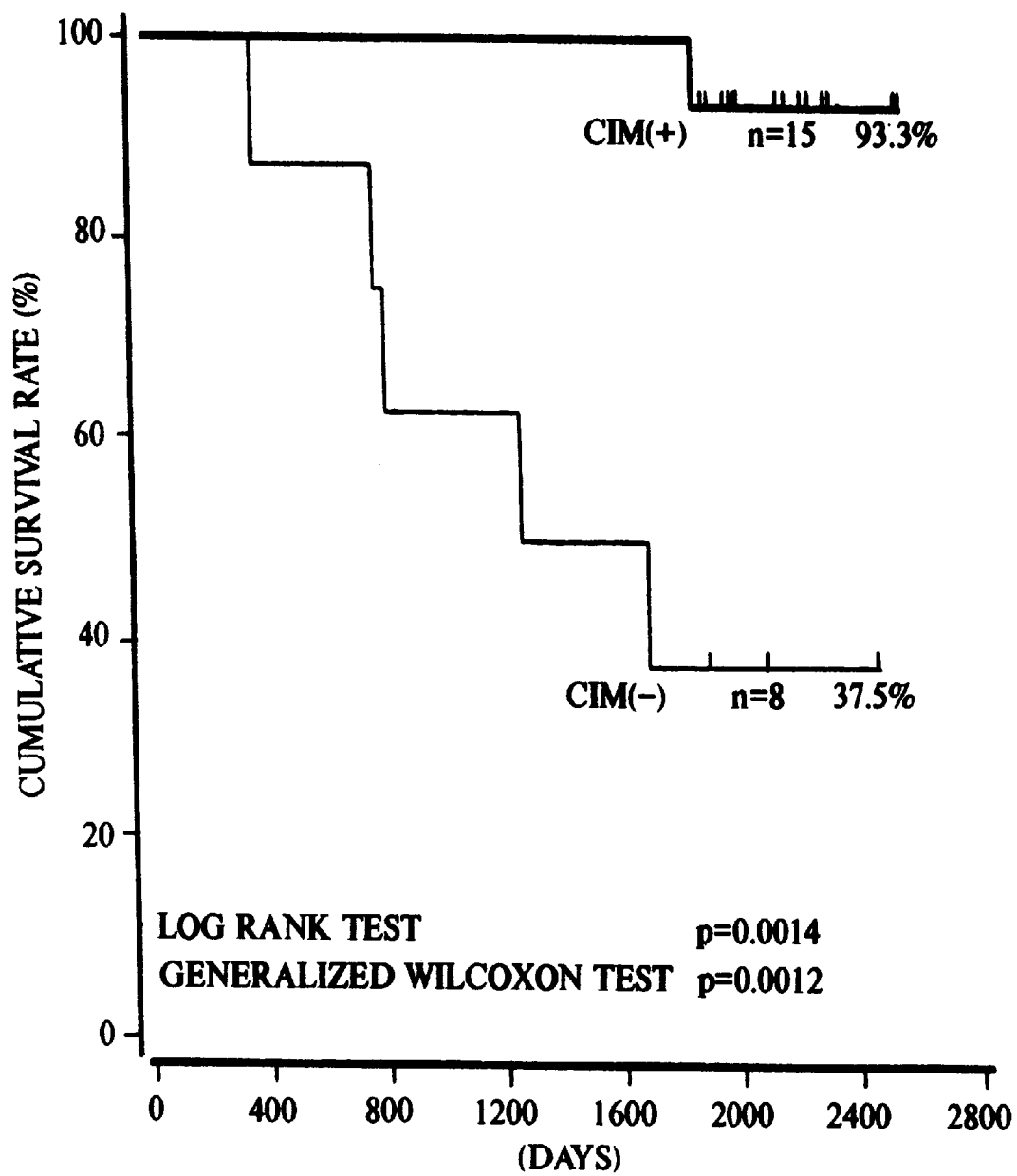
FIG. 9 Cumulative Survival Rate by Kaplan-Meier Method [KM93 Level=3]

In KM93, the 5-year survival rate was 93.3% for the cimetidine group and 37.5% for the control group (Log-Rank test: p=0.0014, generalized Wilcoxon test: p=0.0012) (FIG. 9).

Figure 10:
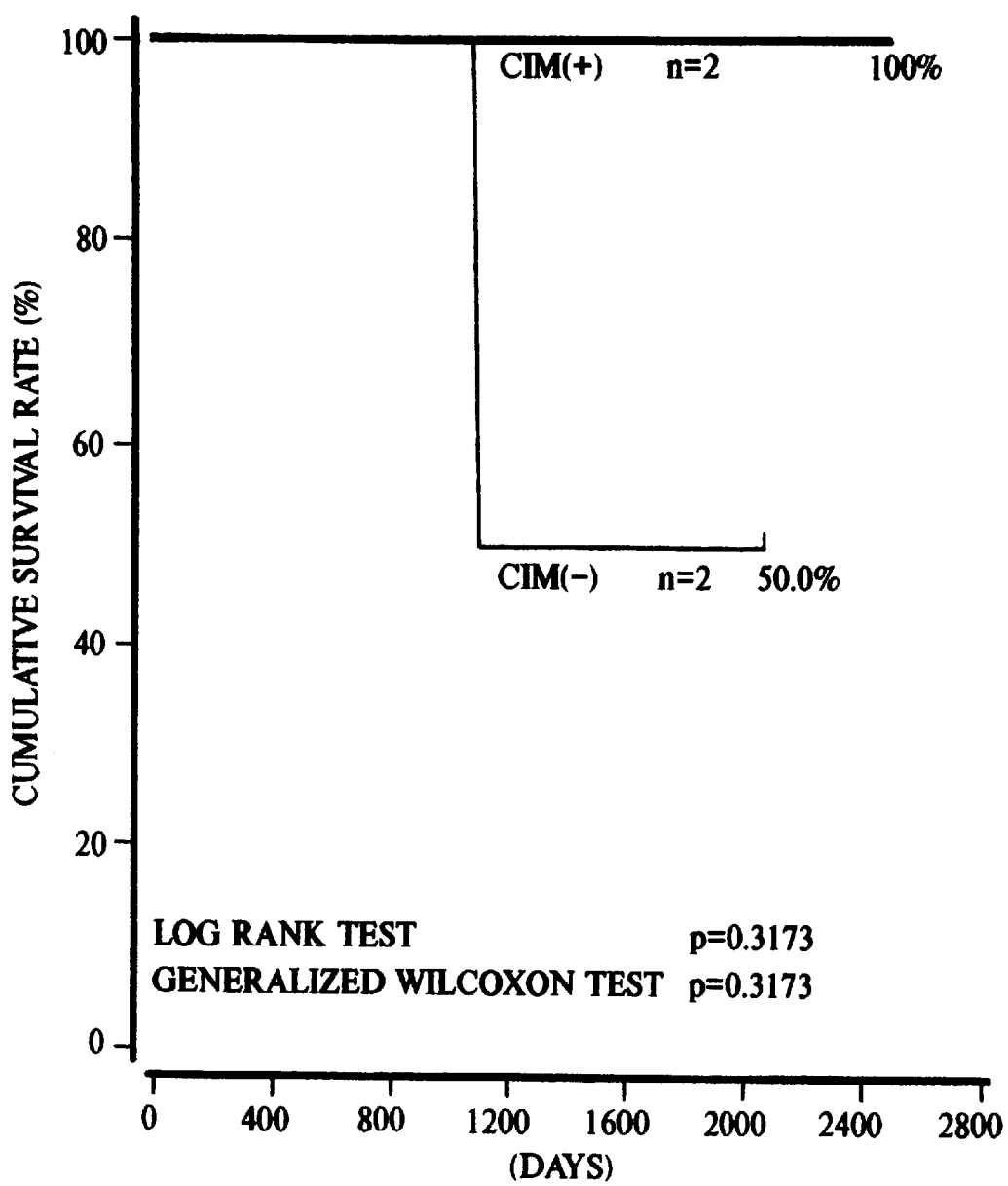
FIG. 10 Cumulative Survival Rate by Kaplan-Meier Method [FH6 Level=3]

In FH6, the 5-year survival rate was 100.0% for the cimetidine group and 50.0% for the control group)(Log-Rank test: p=0.3173, generalized Wilcoxon test: p=0.3173) (FIG. 10).

Figure 11:
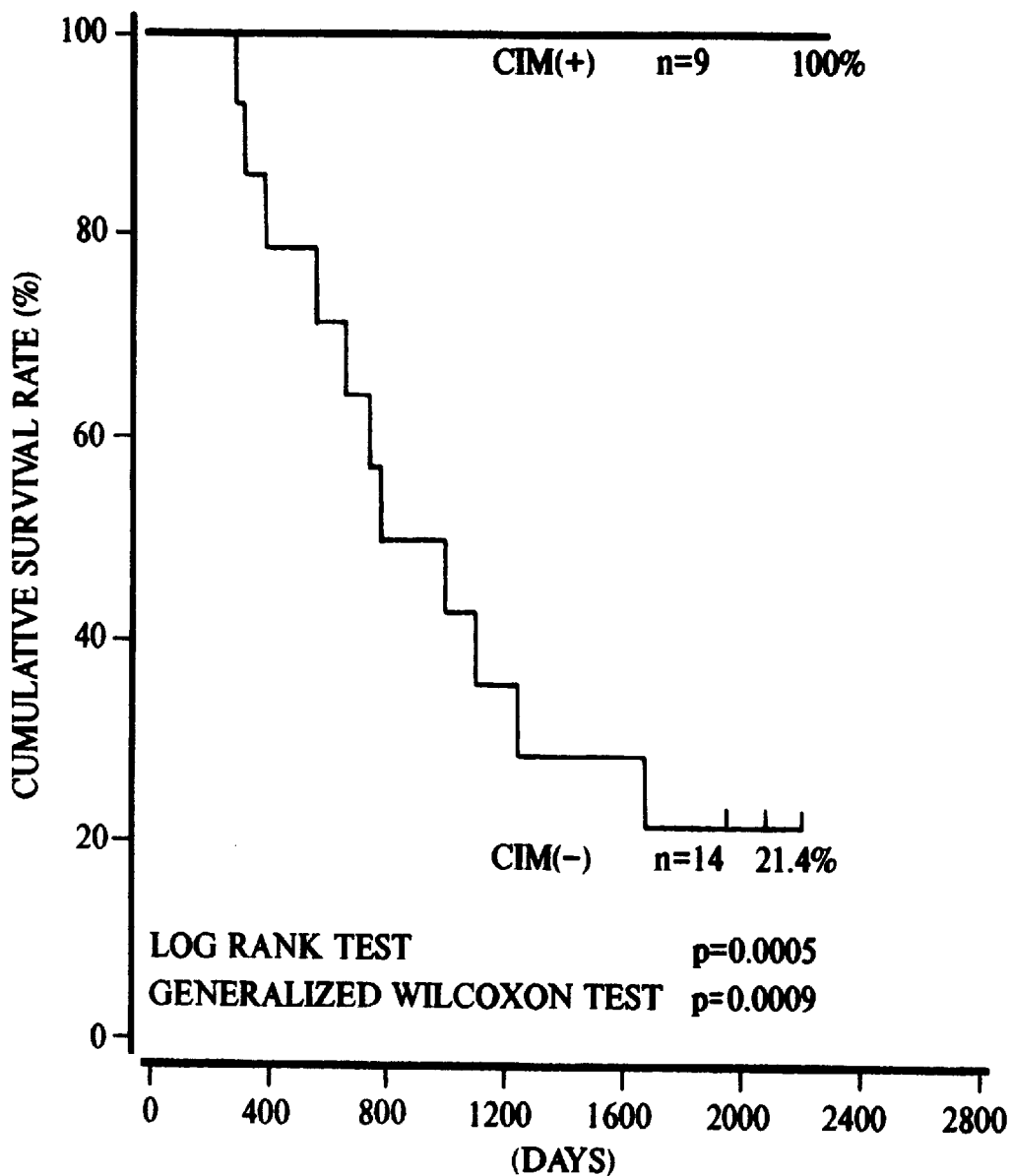
FIG. 11 Cumulative Survival Rate by Kaplan-Meier Method [CA19-9 Level=3]

In CA19-9, the 5-year survival rate was 100.0% for the cimetidine group and 21.4% for the control group (Log-Rank test: p=0.0005, generalized Wilcoxon test: p=0.0009) (FIG. 11).

For purposes herein the terms "CSLEX", "KM93", "FH6" and "CA19-9" refer to specific antibodies used for the detection by the avidin-biotin peroxidase complex (also referred to as "ABC") method of antigens, such as the sialyl Lewis X and A bearing a cancer cell. These antibodies have a different component from each other and are expressed herein as an abbreviation. The ABC method is well known in the art, and can be found in J. Histochem. Cytochem., 30, 157–161 (1982) whose disclosure is incorporated herein by reference.

There has been previously several studies that cimetidine has different effects than other $H_2$ receptor antagonist effects, such as an effect on histamine metabolism (Garcia-Caballero, et al., Adv. BioSciences 89, 273–287 (1993)), or lymphocyte subpopulation (Hansbrough, et al., Am J Surg. 151:249–255 (1986)); or natural killer cell activity (Katoh, et al., Lancet 348:404–405 (1996)); or an effect as antioxidant (Kimura et al., Inorg. Chem. 25, 2242–2246 (1986)). None of these are enough to explain the mechanism of survival benefit conferred upon by administration of cimetidine.

In order to study the mechanism of action of cimetidine to explain this difference, an in vitro analysis of the effect of cimetidine on the human umbilical vein endothelial cell (HUVEC) system was performed. This analysis showed that cimetidine inhibited the expression of E-selectin. This inhibition of cimetidine against the adhesion of cancer cells to vascular endothelial cells results in the novel use of cimetidine for the treatment of, or protection against metastasis of cancer cells.

In metastasis, cancer cells which are released into the blood stream are considered first to adhere to vascular endothelia before proliferating in the extravascular space. In other words, in the process of metastasi of a cancer cell, a certain antigen on a surface of a cancer cell attacks the E-selectin which has appeared on the surface of a vascular endothelial cell and they bind strongly to each other and then proceed onto the next process for metastasis. If E-selectin does not appear on the surface of a vascular endothelial cell, an antigen such as the described sialyl Lewis X and A antigens of a cancer cell, can not adhere to a surface of the vascular endothelial cell. Therefore, no metastasis of the cancer cell is believed to occur.

In a clinical setting, colorectal cancer with sialyl Lewis X expression has been shown to have a higher rate of metastasis (Nakamori, et al., Supra). When cimetidine inhibits the expression of E-selectin, the ligands of sialyl Lewis X and sialyl Lewis A antigen-bearing cancer cells are incapable of attaching themselves to the vascular wall. The present invention demonstrates that that cimetidine inhibited metastasis in patients whose specimens stained strongly for sialyl Lewis X and sialyl Lewis A antigens. These data are significant for cimetidine treatment started two weeks postoperatively. Therefore. one aspect of the present invention is the treatment of cancer patients who stain positively for sialyl Lewis X and sialyl Lewis A antigens and in whom the administration of cimetidine starts within a 2 week postoperative time frame.

Another aspect of the present invention, therefore, is treatment for inhibition or slowing of, or the prevention of, metastatisis in a patient in need thereof, which treatment comprises the adminsitration either pre-operative or immediately postoperative for patients who test positive for the sialyl Lewis X and sialyl Lewis A antigens, with an effective amount of cimetidine.

These data also suggested that cimetidine will inhibit metastasis of other kinds of tumor which bear the sialyl Lewis X or A antigens, for instance in gastric cancer, pulmonary cancer, biliary tract cancer, pancreatic cancer, uterine cancer, ovarian cancer and breast cancer. Therefore, another aspect of the invention is the treatment of tumors which bear the sialyl Lewis X or A antigens, or inhibition of metastasis in patients who stain positively for the sialyl Lewis X or A antigens which method comprises administration of an effective amount of cimetidine. The administration of cimetidine may be either pre-operative, immediately postoperative or even starting at two weeks postoperatively for a period of time to sufficient to inhibit tumor growth or decrease the rate of metastasis in said patients.

These data is a new finding on the inhibition of the adhesion molecule expression, E-selectin, by the agent cimetidine. This finding will open the door towards a new strategy to inhibit the metastasis of the cancer cells in patients which cancers bear the sialyl Lewis X or A antigens or both.

It is recognized that the effects of cimetidine on P-selectin, or L-selectin still remain unknown.

Methods of Immunostaining

Patients of Immunostaining and Methods

A paraffin embedded specimen should be collected in 32 cases for the cimetidine group and in 29 cases for the control 5-FU group. We were unable to collect three specimens because over five years had passed since the operation. Statistical analyses were performed by using Fisher's exact test with a significance level of 0.05.

Sialyl Lewis X and A Antigen Expression by Immunostaining

Paraffin blocks of the surgical specimens were analyzed by using the ABC immunostaining methods (ABC: avidin biotin complex method) to detect the expression of sialyl Lewis X antigens (CSLEX; Signet Lab. Dedham, Mass. KM93; Kyowa Japan, and FH6; Otsuka Japan.), ligands for E-selectin, and of sialyl Lewis A antigen (CA 19-9; Cia Bio International).

Paraffin sections were dewaxed in xylene, dehydrated through graded alcohol, and washed with distilled water. After 10 minutes treatment with normal calf serum albumin, the monoclonal antibody was incubated on each section for two hours and rinsed off with phosphate buffered saline (PBS). The biotinylated anti-mouse immunoglobulin (Vactastain) was incubated on each section for 30 minutes and then washed with PBS. Endogenous peroxidase was blocked by immersion in 0.3% (w/v) hydrogen peroxide in absolute methanol for 20 minutes and then washed with PBS. Avidin-biotinylated horseradish peroxidase was then applied for 30 min followed by washing with PBS. Sections were incubated for 1 to 5 min in a peroxidase substrate solution (mixture of 0.02% diaminobenzidine tetrahydrochloride and 0.065% NaN3, in a 0.003% hydrogen peroxide added in Tris buffer solution). After washing with distilled water, the sections were counterstained with hematoxylin, dehydrated in ethanol, washed in xylene, and then mounted.

The level of immunostaining of cancer cells was graded into four categories: level 0, no staining; level 1, 5% or less staining; level 2, 5–70% staining, and level 3, 70% or more staining. A comparative analysis was performed with respect to the level of immunostaining, metastasis and treatment. Statistical analysis was done by using Fisher's equation, with small P values less than 0.05 being significant.

Patients and Survival of Colorectal Cancer

Eligible patients had a histological diagnosis of colorectal cancer, were younger than 75 years and had a primary tumor assigned as either $T_2$ or $T_3$. All patients underwent macroscopic curative resection. Patients were excluded preoperatively if they had undergone any radiotherapy, chemotherapy, or immunotherapy, or, if they had multiple cancer or severe complications.

Seventy-two patients were enrolled in the trial in a 2 year period. Eight patients were found to be ineligible. In 5 patients the stage of the disease was inappropriate for this trial, in 2 patients cimetidine was not administered and in 1 patient famotidine was administered. The cimetidine group comprised 34 patients and the control group 30 patients. Both treatment groups were well balanced concerning the following clinical pathological characteristics: age, sex, stage, macroscopic shape, size, location, pathological type, lymph node metastasis and distant metastasis.

The cimetidine group of patients (n=34) received 8 mg/m² of intravenous mitomycin (Kyowa Hakko, Inc., Japan) within 24 hours postoperatively and 800 mg/day p.o. of cimetidine (SmithKline Beecham Co., Japan) and 200 mg/day of 5-FU (Kyowa Hakko, Inc., Japan) for one year, starting two weeks following curative operation. The cimetidine group was compared with the control group who received the same treatment except for cimetidine (n=30).

Survival was the primary endpoint. Time to recurrence (disease-free interval) was also assessed. Survival curves were generated by using the Kaplan-Meier method. The log-rank test was used to compare the distribution of survival and the disease-free interval, with a significance level of 0.05

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows:

What is claimed is:

1. A method of selecting a group of colorectal cancer patients for cimetidine treatment, said method comprising
   1) testing the patients cancer cells for the presence of sialyl Lewis X antigen or sialyl Lewis A antigen; and
   2) selecting those patients whose cancer cells test positively for the presence of either sialyl Lewis X antigen, or sialyl Lewis A antigen or both sialyl Lewis X and A antigen, for cancer treatment.

2. The method according to claim 1 wherein the patients who have been selected have levels 2 and 3 immunostaining for sialyl Lewis A antigen.

3. The method according to claim 1 wherein the patients who have been selected have levels 2 and 3 immunostaining for sialyl Lewis X antigen.

4. The method according to claim 1 wherein the patients who have been selected have levels 2 and 3 immunostaining for sialyl Lewis X and A antigen.

5. The method according to any one of claims 1–4 wherein the patients who have been selected are treated with an amount of cimetidine effective to treat colorectal cancer.

6. The method according to claim 5 wherein the administration of cimetidine for treatment of the patients who have been selected starts within a 2 week postoperative time period.

7. The method according to claim 5 wherein the administration of cimetidine is given pre-operatively to said patients who have been selected.

8. The method according to claim 6 wherein the administration of cimetidine is given immediately postoperatively to said patients who have been selected.

* * * * *